United States Patent [19]

Armeniades et al.

[11] Patent Number: 4,722,350
[45] Date of Patent: * Feb. 2, 1988

[54] OPHTHALMIC INSTRUMENT FOR MEASURING INTRAOCULAR FLUID PRESSURE

[76] Inventors: C. D. Armeniades, 2127 Addison Rd., Houston, Tex. 77030; Louise C. Moorhead, 3803 University Blvd., Houston, Tex. 77005

[*] Notice: The portion of the term of this patent subsequent to Oct. 22, 2002 has been disclaimed.

[21] Appl. No.: 775,257

[22] Filed: Sep. 16, 1985

Related U.S. Application Data

[63] Continuation-in-part of Ser. No. 653,723, Sep. 21, 1984, abandoned, which is a continuation-in-part of Ser. No. 436,953, Oct. 27, 1982, Pat. No. 4,548,205.

[51] Int. Cl.⁴ ............................................. A61B 5/02
[52] U.S. Cl. .................................. 128/748; 128/645
[58] Field of Search ................ 128/748, 645, 675, 676

[56] References Cited

U.S. PATENT DOCUMENTS

| | | |
|---|---|---|
| 3,088,323 | 5/1963 | Welkowitz et al. |
| 3,550,583 | 12/1970 | Chiku . |
| 3,553,625 | 1/1971 | Stedman . |
| 3,572,319 | 3/1971 | Bittner et al. |
| 3,710,781 | 1/1973 | Huthcins, IV et al. |
| 3,863,504 | 2/1975 | Borsanyi . |
| 3,865,100 | 2/1975 | Kanai et al. |
| 3,939,823 | 2/1976 | Kaye et al. |
| 3,941,122 | 3/1976 | Jones . |
| 3,946,724 | 3/1976 | La Balme . |
| 4,019,514 | 4/1977 | Banko . |
| 4,023,562 | 5/1977 | Hynecek et al. |
| 4,091,682 | 5/1978 | Abbott et al. |
| 4,117,843 | 10/1978 | Banko . |
| 4,168,707 | 9/1979 | Douvas et al. |
| 4,180,074 | 12/1979 | Murry et al. |
| 4,274,411 | 6/1981 | Dotson . |
| 4,274,423 | 6/1981 | Mizuno et al. |
| 4,281,667 | 8/1981 | Cosman . |
| 4,395,258 | 7/1983 | Wang et al. |
| 4,548,205 | 10/1985 | Armeniades et al. ............... 128/748 |

FOREIGN PATENT DOCUMENTS 3234621.2 3/1984 Fed. Rep. of Germany .

*Primary Examiner*—Edward M. Cover
*Attorney, Agent, or Firm*—Pravel, Gambrell, Hewitt, Kimball & Krieger

[57] ABSTRACT

An ophthalmic device and system for measuring and controlling relative pressure of fluid inside an ocular globe includes a surgical instrument which is adapted to penetrate the ocular globe. A fluid pressure transducer is mounted on the instrument so that, when the instrument penetrates the ocular globe, the transducer is located adjacent to an opening that communicates with the interior of the globe so that it can react to pressure changes in the fluid therein and generate signals in response to pressure changes in the fluid. The signal is transmitted external of the instrument to a pump or other fluid transfer device which is operatively connected to the transducer for first receiving signals and then supplying or removing fluid from the ocular globe in response to the signals according to a predetermined set of instructions. The pump is connected to a closed loop in which fluid is continuously circulated. Fluctuations in intraocular pressure cause the pump to speed up or slow down and then supply fluid to or remove fluid from the ocular globe through a conduit connected to the closed loop.

7 Claims, 10 Drawing Figures

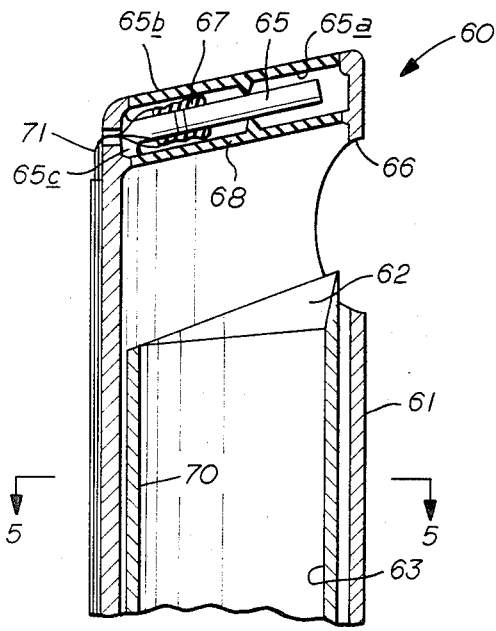
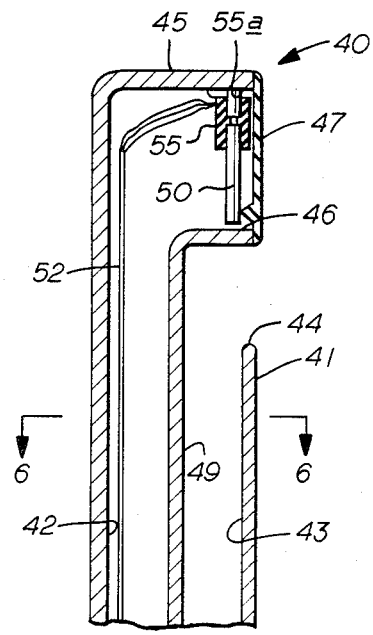
FIG. 3  FIG. 4
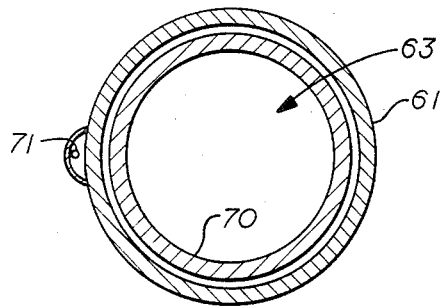
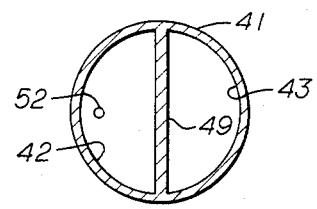
FIG. 5  FIG. 6

OPHTHALMIC INSTRUMENT FOR MEASURING INTRAOCULAR FLUID PRESSURE

BACKGROUND OF THE INVENTION

1. Field of Invention

The present invention relates to ophthalmic microsurgical instruments and, more particularly, to such surgical instrumentation which continuously monitors and controls internal ocular globe fluid pressure during ophthalmic surgical procedures and the like.

2. General Background

A large number of microsurgical procedures inside the eye are performed through "closed systems" which maintain the integrity and internal pressure of the ocular globe while microsurgical instruments are used to penetrate the eye through one or more small incisions (see FIG. 1). Exemplary functions performed by these instruments are:

Fragmentation—the cutting and separation of ocular tissue, such as the lens in cataract surgery or fibrous and membrane-like growths inside the vitreous (e.g., vitrectomy, membranectomy);

Emulsification—the mechanical digestion of tissue (usually the lens) by means of ultrasound in order to facilitate its removal through small incisions;

Irrigation (infusion)—the introduction of a saline solution into the operating field by means of gravity or positive pressure; and Aspiration (suction)—the removal of fluid and/or entrained tissue fragments by means of vacuum.

The surgeon combines irrigation and aspiration to transport tissue fragments away from the operating field. He or she also uses these functions to maintain intraocular pressure during the surgical procedure. Control of pressure in irrigation and aspiration is extremely important. If the aspiration suction is too strong (due to excessive vacuum) it may damage endothelial cells during anterior chamber surgery or may cause retinal detachment in vitrectomy procedures. Too high an irrigation pressure or excessive variations in the pressure or flow rate of the irrigation fluid may traumatize ocular tissue.

With traditional instrumentation the level of irrigation flow and range of aspiration vacuum are adjusted by a surgical assistant in response to the surgeon's instruction. Available systems afford the surgeon direct control of these variables, usually by means of fingertip or footpedal switches, and provide visual or audio indications of aspiration pressure (vacuum) and irrigation flow. See, for example, U.S. Pat. No. 4,168,707 entitled "Control Apparatus for Microsurgical Instruments."

Generally, such pressure sensors are located in a remote instrument console located a distance of 1–2 meters from the operating site and connected to it through thin, flexible plastic tubing containing a saline solution. Such remote monitoring of pressure has the potential of introducing significant errors in pressure measurements due to the compliance of the tubing and the inertia and viscosity of the fluid column interposed between the surgical site and pressure sensor location. Such errors become more pronounced when air bubbles and tissue fragments enter the flexible conduit which transmits fluid between the operative site and instrument console.

Since a surgeon must depend primarily on visual observation and feel of the surgical site to guide him in controlling the level of suction and irrigation flow rate, knowledge of the accurate pressure or vacuum forces exerted on the tissue at the operating site would enhance greatly the ease and safety of the procedure. Furthermore, accurate control of intraocular pressure both during intraocular surgery and at the time of final wound closure would help minimize postoperative overpressure and associated dangers to the patient.

While there are many devices which are associated with ophthalmic surgical procedures, none is known which accurately monitors internal ocular pressure during surgery. For example, Russian patent 733,670 teaches the use of a strain gauge in the cutting tip of an ophthalmic surgical instrument and a variable audible signal is generated in response to tissue pressure encountered by the instrument when cutting, but internal pressure is not measured.

U.S. Pat. No. 3,945,375 is directed to an ophthalmic surgical instrument for removing tissue and includes a rotating fluted cutter housed in a probe adapted to be inserted into a portion of the body from which tissue is to be removed. The instrument can supply irrigation fluid through the probe to the area being operated upon and evacuate the material through the probe after being engaged by the cutter, but does not monitor internal pressure.

U.S. Pat. No. 4,117,843 teaches a system which controls the infusion of fluid to a closed operating field such as an eye at a selected predetermined pressure in addition to being able to sever material in the field and for evacuating the severed material in a suspension or emulsion of the infusion fluid. However, internal pressure is not measured.

U.S. Pat. No. 4,168,707 relates to an electronic control for microsurgical instruments which is adapted for use in intraocular surgery. Commands received from a surgeon's foot control unit control the various aspiration functions normally performed manually by a surgical assistant. A typical control system used to perform the infusion and aspiration functions required during intraocular survey is described in detail.

There are also various patents which deal with strain gauges that are used to measure blood pressure. See, for example, U.S. Pat. Nos. 2,959,056; 3,550,583; 3,946,724; and 4,274,423. Blood pressure transducers implantable in arteries or veins are described in U.S. Pat. Nos. 3,724,274 and 3,748,623. U.S. Pat. No. 4,274,423 teaches a catheter for use in determining pressures within blood vessels and the heart. And U.S. Pat. No. 4,175,566 is directed to a fluid velocity flow probe.

U.S. Pat. No. 3,776,238 relates to an instrument with two tubes that are mounted co-axially within one another with an opening adjacent the end of the outer tube. Cutting of the vitreous and fibrous bands in the eye caused by hemorrhaging is performed by a chopping action of the sharp end of the inner tube against the inner surface of the end of the outer tube and the bands are removed by suction through the inner tube. The removed vitreous is continuously replaced by a saline solution introduced into the eye through the instrument.

None of these prior art devices provides an ophthalmic microsurgical instrument which can safely and accurately monitor or control internal fluid pressure during ophthalmic surgery.

SUMMARY OF THE PRESENT INVENTION

The subject invention is directed to a device and system for measuring and controlling fluid pressure within the ocular globe during opthalmic surgery.

The apparatus of the present invention senses the intraocular pressure exerted on the tip of the microsurgical instrument or local suction forces on tissue removed through aspiration. An electric signal generated in response to relative pressure changes can be used to regulate automatically aspiration vacuum level or irrigation flow rate within acceptable ranges for providing an extra measure of safety to those surgical procedures.

The instrument includes a needle-like instrument with a pressure transducer mounted so that, when the instrument penetrates the ocular globe, the transducer lies either immediately outside the globe or inside the globe, where it can communicate directly with the fluid therein. The transducer is capable of measuring either the pressure of ocular fluid surrounding the instrument relative to ambient atmospheric pressure or local suction forces in the instrument opening exerted on diseased tissue as the tissue is aspirated.

The ocular instrument utilizes a miniature pressure sensor located adjacent to a thin, flexible diaphragm. The diaphragm can be constructed from natural rubber or other suitable elastomer and serves as a barrier between the fluid, the pressure of which is to be measured, and some appropriate reference environment. The diaphragm is connected to the transducer and operates to transmit forces to the transducer as a result of pressure differences between these two environments causing the diaphragm to move.

The transducer is a suitable, miniaturized pressure transducer with appropriate sensitivity and stability. An electric signal is generated by the transducer, which is transmitted to an instrument console where it is amplified and displayed. The signal can be used to activate known feedback control circuits to operate a valve for regulating or limiting suction vacuum or irrigation fluid flow through the same or another instrument.

One system in which the instrument can be used includes a closed loop through which a pump continuously circulates a saline solution compatible with intraocular fluid. When the transducer detects pressure fluctuations in the eye outside a predetermined range, the signals generated by the transducer, which are received by a microprocessor controller, cause the pump to speed up or slow down for changing the fluid pressure in the closed loop and causing fluid to be supplied to or removed from the eye through a conduit that is connected to the closed loop.

Accordingly, it is an object of this invention to provide an ophthalmic surgical instrument which accurately and safely measures the pressure exerted by ocular fluids or tissues at the site of microsurgical activity.

Another object of the invention is to provide an accurate pressure valve signal to feedback control circuits which automatically regulate and/or limit suction vacuum or regulate the flow and pressure of the irrigation fluid responsive to sensed intraocular pressure.

The instrument which is the subject of the present invention provides a number of controls during anterior chamber or cataract surgery such as, for example: (1) control of anterior chamber depth (space between cornea and iris); (2) better regulation of bleeding by precise pressure tamponade; (3) accurate measurement of intraocular pressure through a second site during wound closure; (4) better control of suture tension during wound closure to avoid astigmatism; and (5) better approximation of physiologic intraocular pressure after wound closure.

Controls afforded by the invention during vitreous surgery include: (1) measurement and control of aspiration forces applied to diseased tissue at the instant of excision and limitation of these forces to avoid retinal detachment; (2) regulation of vitreous pressure from a second site in order to control bleeding during surgery; and (3) better approximation of physiologic intraocular pressure after wound closure.

BRIEF DESCRIPTION OF THE DRAWINGS

For a better understanding of the nature and objects of the present invention, reference should be had to the following detailed description, taken in conjunction with the accompanying drawings, in which:

FIG. 3 is a sectional view of one embodiment of the invention where a pressure transducer is mounted to provide communication between the interior of the ocular globe and an internal conduit of an instrument of the type shown in FIG. 2;

FIG. 4 is another embodiment of the invention in which the transducer communicates directly with the interior of the ocular globe;

FIG. 5 is a sectional view looking along lines 5—5 of FIG. 3;

FIG. 6 is a sectional view looking along lines 6—6 of FIG. 4;

DETAILED DESCRIPTION OF PREFERRED EMBODIMENTS

Figure 1:
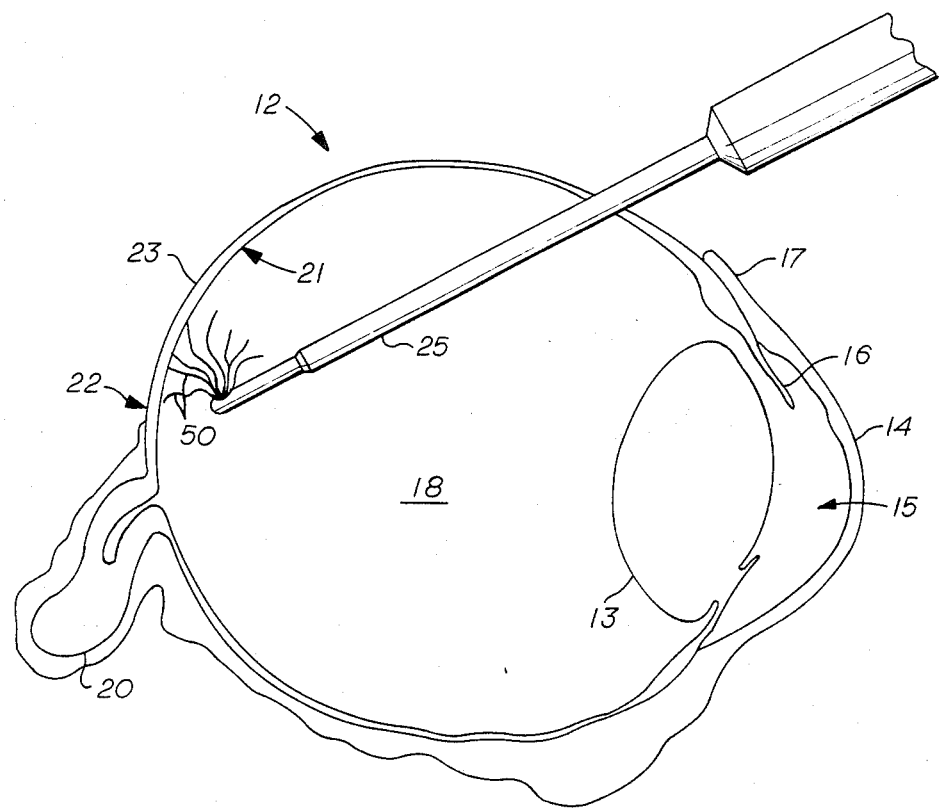
FIG. 1 is a schematic section view illustrating a "closed system" surgical procedure in the eye.
Figure 2:
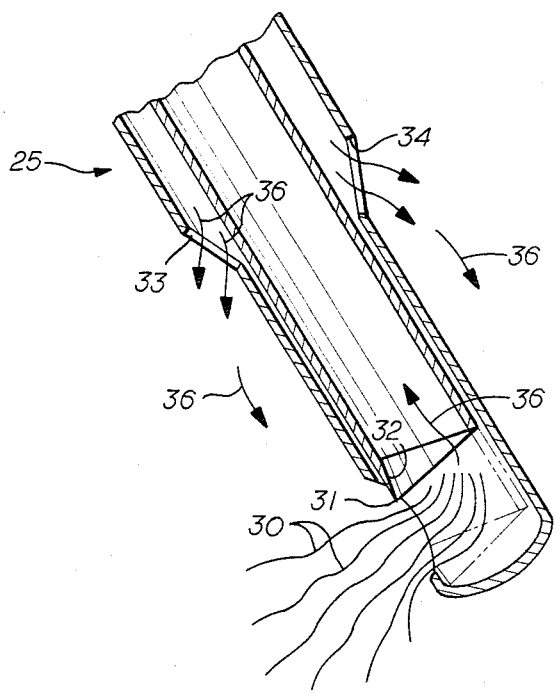
FIG. 2 is a sectional view of the tip of a microsurgical instrument for performing vitreous surgery which is known in the prior art.

FIG. 1 illustrates an ocular globe or eye 12 which includes a lens 13, cornea 14, anterior chamber 15, iris 16, ciliary body 17, vitreous body 18, optic nerve 20, retina 21, sclera 22 and choroid 23. An instrument 25, the tip of which is shown in greater detail in FIG. 2, is a surgical needle 0.4 to 1.0 mm in outside diameter formed of stainless steel which is attached to a handpiece (not shown) for manipulation by the surgeon. The handpiece can be connected through flexible plastic tubing (not shown) to both a saline solution reservoir for irrigation (not shown) and a pumping system for aspiration (not shown). The details of elements not shown are known to those with ordinary skill in the art and need not be described in detail in order to practice the invention.

The instrument 25 is a known irrigation/aspiration/cutting tip and is shown in FIG. 1 as being inserted in the vitreous 18. Suction is used to aspirate diseased tissue 30 into a side opening 31 of the instrument 25. As shown best in FIG. 2, the tissue is cut by a curved microguillotine blade 32 which is actuated by the surgeon and slidable in the instrument 25. A saline solution or the like is discharged through outlets 33, 34, and infuses the operation site. The infusion, in combination with controlled suction through the opening 31, helps to draw the tissue fragments 30 into the instrument 25 for removal after they are cut by the blade 32. Arrows 36 in FIG. 2 illustrate both the discharge of saline solution and suction action mentioned above.

The conventional instrument shown in FIGS. 1 and 2, however, has no provisions for accurately measuring the local suction force used to draw the diseased tissue 30 into the instrument 25 prior to cutting. Since the tissue removed by the vitrectomy procedures is usually located in the immediate vicinity of the retina 21, the danger of inadvertent damage to the retina 21 or other healthy tissue by excessive suction force during vitrectomy is considerable.

The embodiment of the invention illustrated in FIGS. 3 and 5 solves this problem by enabling the suction force to be monitored constantly. An instrument similar to the one in FIGS. 1 and 2 has been modified to measure pressure differences between the external and internal forces of its cutting/aspiration tip. The modified instrument is referred to generally by reference numeral 60 and includes an outer elongated housing 61 which surrounds an inner concentric guillotine 70 which carries a cutting blade 62 that cooperates with an opening 66 for surgically removing tissue fragments as described above. An inner bore or channel 63 operates to convey fluids and/or tissue. Only the tip of such an instrument is shown in FIG. 3 and additional features such as the discharge outlets 33, 34, shown in FIG. 2 were omitted to simplify the description.

A pressure transducer 65 is mounted in a chamber 65a located near aspiration inlet 66, the chamber 65a being bounded by two parallel diaphragms 67, 68, formed of silicon rubber inserts that are about 1 mm in diameter. The diaphragms 67, 68, are connected to the instrument 60 by means of an epoxy resin. The transducer 65 is preferably mounted at the outer end 61(a) of the tip of the housing 61.

Pressure transducer 65 is a piezo-electric or photoelectric device known to the art which is capable of measuring intraocular pressure with the required sensitivity ($\pm 1$ mm. Hg), stability and linearity. Other types of transducers, such as sensors operating in conjunction with fiber-optic light guides which transmit signals in the form of variations in light intensity caused by pressure differences moving a reflective surface, can also be used in conjunction with the invention without substantially altering the size, shape or function of the instrument. An electrical signal generated by the transducer 65 is carried through wire leads 71 to a monitor/console which is known in the art and contains a suitable power supply as well as the necessary electrical circuits for conditioning, amplifying and displaying the pressure measurement.

The piezoelectric elements 65(b) are attached to a cantilever beam and a rigid base 65c, which is anchored to the wall of the instrument. Wire leads 71, which carry electrical signals from the transducer 65, are connected to the exterior surface of the instrument 60 so as to avoid interference with the action of the guillotine cutter 70. The leads 71 are bonded to the instrument 60 so that they are part of its smooth outer surface.

The vitrectomy suction instrument 60 significantly enhances safety through sensitivity to suction force and consequently intraocular pressure during surgery. As the surgeon aspirates strands of diseased tissue into the opening 66, the local pressure difference measured between diaphragms 67, 68, by the transducer 65 results in a relative pressure reading that reflects the forces exerted on the tissue strands as they enter the aspiration inlet 66. These forces fluctuate continuously because of differences in the viscoelastic properties of the manipulated tissue and the viscosity of the surrounding vitreous. The force level at any given time can fall in a range that departs considerably from the average force and the pressure in the vacuum line can be adjusted to accommodate these fluctuating force levels.

By using the transducer 65, a signal can be generated to activate momentarily a vacuum relief valve in a known way (not shown) when the local pressure exceeds preset levels to adjust the suction when the force level falls outside the permissible range. Thus, the instrument 60 operates to reduce considerably the danger of damage to healthy tissue by preventing excessive instantaneous peaks in local suction forces.

Referring to FIGS. 4 and 6, another embodiment of the invention is illustrated, this one being directed to a surgical instrument which can measure intraocular pressure while performing an irrigation or aspiration procedure. The instrument is generally designated by reference numeral 40 and is an elongated body 41 formed of surgical grade stainless steel with an outside diameter of approximately 1 mm. The body 41 is divided through substantially its entire length into two parallel channels 42, 43, that are separated by an internal wall 49. Channel 43 is an irrigation/aspiration channel which is connected through a handpiece (not shown) to either a vacuum system (not shown) or a saline supply reservoir. The channel 43 has an outlet 44 located near the apex 45 of the tip of the instrument 40.

A transducer 50 is mounted in the portion of the channel 42 adjacent to the tip of the instrument 40, the channel 42 being vented to the atmosphere at a suitable site away from the operating field. The transducer 50 is of the type described above for the embodiment of FIGS. 3 and 5 and is connected to the instrument 40 through a base 55a. At the tip of the instrument 40, the transducer channel 42 terminates at a window 46 which is located adjacent to the outlet 44. The window 46 is approximately 1 mm in diameter and is fitted with a diaphragm 47 formed of silicon rubber. The diaphragm 47 is connected to the window 46 by means of epoxy resin. Wire leads designated by reference numeral 52 carry electrical signals generated by the transducer 50 to suitable instrumentation (such as that described below) for translating the signals into useful information for monitoring and regulating intraocular pressure.

The intraocular pressure probe 40 is suitable for the measurement and control of intraocular pressure during closed system procedures in the anterior chamber 15 as well as in the vitreous chamber 18. The instrument 40 can be inserted at a site separate from the operating incision and remain in place throughout the entire procedure, providing to the surgeon an independent source of determining and/or controlling intraocular pressure for providing information used in tamponade, suture tension controls and final approximation of physiologic pressure at the end of wound closure.

One disadvantage of placing the transducer in the portion of the probe that penetrates the eye, as done in instruments 40 and 60 (see FIGS. 4 and 3, respectively), is that this configuration requires the probe to have a larger diameter than would otherwise be necessary. This problem can be eliminated without significantly affecting the accuracy or speed of the device by relocating both the pressure sensitive diaphragm and the transducer outside the eye but in a position where a significant signal can be generated in response to changes in intraocular pressure.

Figure 7:
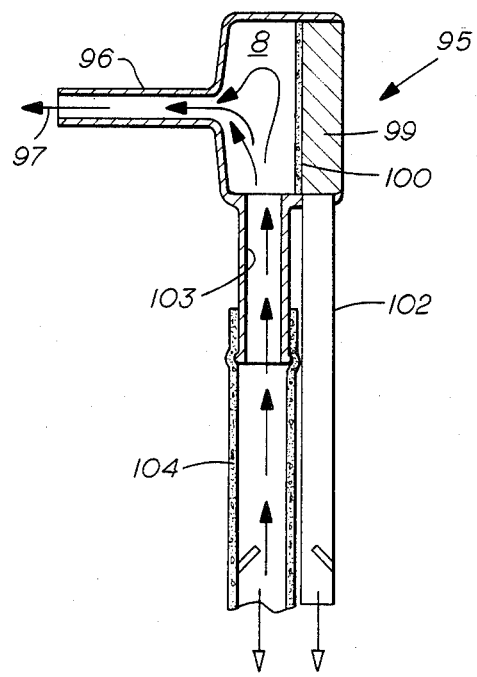
FIG. 7 is a sectional view of another instrument similar to those of FIGS. 3-6, in which the transducer is located outside the eye but adjacent to an opening that communicates with interior of the eye when the instrument penetrates it.

FIG. 7 illustrates one such alternative embodiment of the invention. The instrument, generally designated by reference numeral 95, includes an elongated needle section 96 with an opening 97, which can be inserted into the ocular globe. The opposite end of the needle section 96 opens into a chamber 98 that is designed to remain outside the ocular globe. A transducer 99 is mounted in the chamber 98 opposite the opening 97. Although the transducer 99 is not located inside the ocular globe, its position adjacent to the opening into the globe supplies a pressure reading nearly as accurate as one obtained through internal placement.

The transducer 99 can be of the type described above for the embodiments illustrated in FIGS. 3-6, or a fused silicon type such as Entran Model No. EPIL-F080-55 manufactured by Entran Devices, Inc., Fairfield, N.J., which is separated from the chamber 98 by a diaphragm 100 formed of paralyne or the like. Wire leads 102 carry electrical signals generated by the transducer 99 to external instrumentation that is described in detail below. The chamber 98 is equipped with an input opening 103 that can be connected to a flexible plastic tubing 104 for supplying fluid in appropriate amounts to the ocular globe.

The instruments shown in FIGS. 3-5 and 7 can be incorporated into any number of systems for controlling pressure within the ocular globe 12. For example, the signal generated by the transducer can be used to control the suction level through the same probe on which the transducer is located (FIGS. 1 and 2) or a second probe when the surgical procedure requires fluid to be circulated through the eye. For other surgical procedures, pressure in the eye can be maintained within a predetermined range through a single probe.

Figure 8:
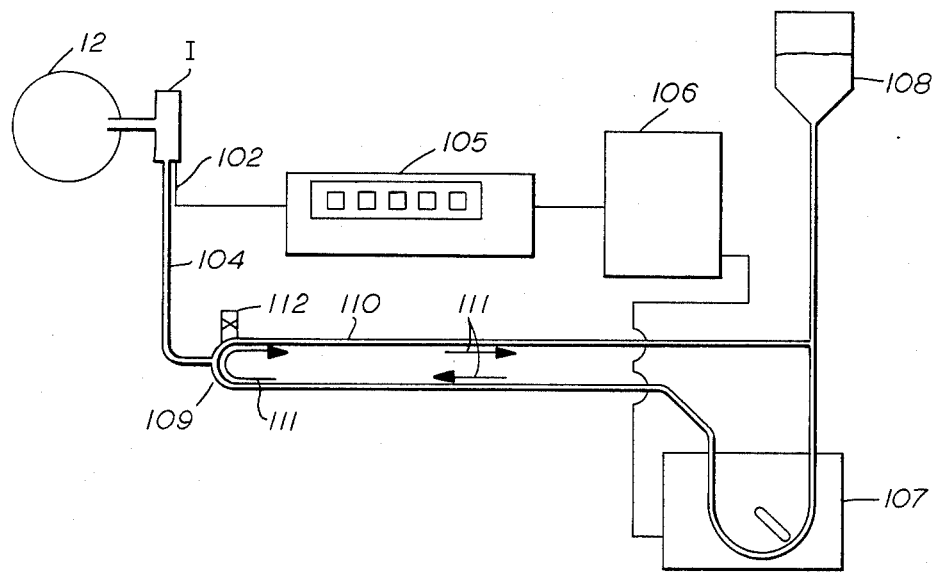
FIG. 8 is a schematic view of an embodiment of the control system which includes the instrument shown in FIG. 9.

The instruments described above can be used in a system of the type shown in FIG. 8 where a pressure level within a predetermined range is maintained and controlled more accurately than in any other known system. This is accomplished through the use of a closed loop through which saline solution is continuously circulated. The loop is connected to the eye so that reaction to a change in pressure detected by the transducer, which speeds up or slows down the circulation, causing fluid to be supplied to or withdrawn from the eye, is virtually instantaneous.

Referring to FIG. 8, an instrument I of the type shown in FIGS. 3-6 or 7 penetrates the ocular globe 12 and is connected to a fluid conduit 104. A flow loop 110 is connected to the conduit 104 through a flow splitter connection 109. When the system is operating, a peristaltic pump 107 continuously circulates saline solution through the loop 110 in the direction of arrows 111. A reservoir of solution 108 is connected to the loop 110 for supplying addition solution when needed. A pressure relief value 112 can be provided at the splitter connection 109, but it is not considered necessary for successful operation of the circuit.

If the instrument 100 detects a pressure change in the ocular globe 12, a signal is transmitted through a line 102 to a monitor/console 105 of a type known in the art, which contains a suitable power supply as well as the necessary electrical circuits for conditioning, amplifying and displaying the pressure measurements. The signal is in turn transmitted to a microprocessor controller 106 of a type known in the art, which is operatively connected to the pump 107.

The microprocessor controller is programmed to allow the pump 107 to circulate fluid through the loop 110 at a predetermined flow rate when signals received from the transducer indicate that the pressure of intraocular fluid is within a preset range. This flow rate will operate to maintain a predetermined pressure level within the ocular globe. However, if a pressure drop is detected by the instrument I, the resulting signal to the microprocessor controller operates to speed up the pump a predetermined amount for infusing additional saline solution into the eye.

Conversely, if a pressure increase is detected, the pump speed is reduced. The use of a flow splitter in relatively close proximity to the instrument 100 (for example, by resting it on the forehead of the patient) and the continuously circulating saline solution in the loop 110 provide for a much more rapid response to pressure changes in the eye than if a long fluid column were used or if a pump had to be activated in response to each pressure change.

Figure 9:
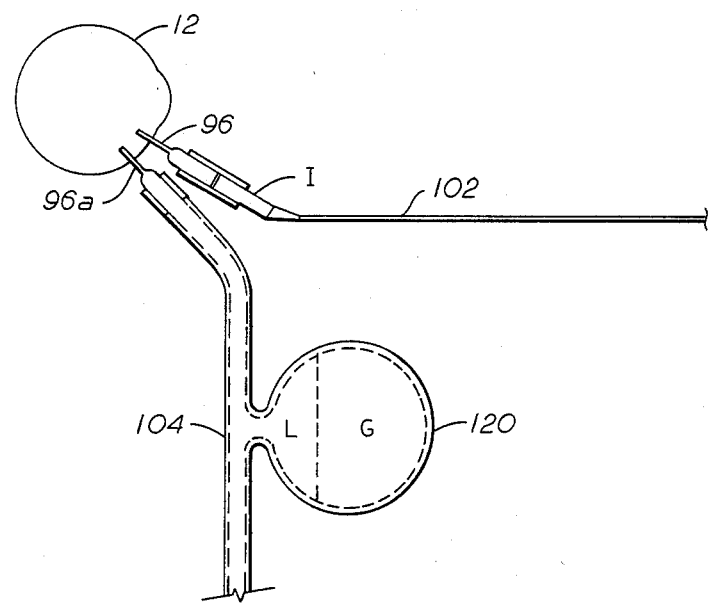
Figure 10:
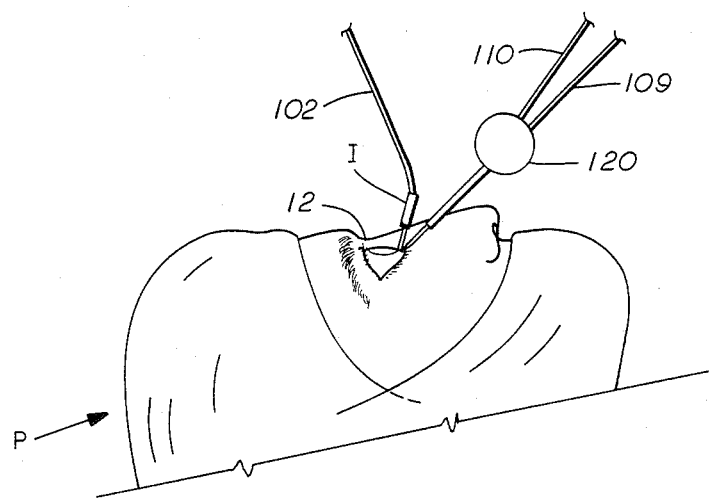

Another embodiment of the invention is shown in FIGS. 9 and 10, where a compliance chamber 120 is connected to the fluid conduit 104, either downstream from the splitter connection 109 (FIG. (9) or at the splitter connection 109 (FIG. 10). The compliance chamber 120 operates to accommodate sudden changes in pressure in the ocular globe 12 caused by surgical manipulations such as pressing on the globe, pulling on the ocular muscles or tightening of stitches where pressure is raised or starting or enlarging an incision where pressure is lowered. Such pressure fluctuations tend to be very rapid, on the order of $10^{-2}$–$10^{-1}$ per second. The normal response time of the system shown in FIG. 8 is not fast enough to react to many such pressure fluctuations because of inertial and frictional forces in the equipment and associated flow lines.

In order to provide a quicker response time to these sudden fluctuations, the compliance chamber 120 is included in the flow line leading to the eye, in close proximity to eye. Preferably, the compliance chamber 120 is located from 6–10 cm. from the tip of needle section 96a.

The compliance chamber 120 is formed as a small, spherical chamber that is 4–8 cm. in diameter with highly elastic walls. The compliance chamber 120 can be completely filled with the fluid F flowing through the flow lines 102, 104 (FIG. 10). However, the reaction time to intraocular pressure changes can be increased by initially filling the chamber 120 with air or other gas G, as shown in FIG. 9, for more rapidly accommodating pressure changes because of the greater compressibility of the gas G.

As shown in FIG. 9, the compliance chamber 120 can be formed as part of or connected to the conduit 104, downstream from the splitter connection 109. In such case, the conduit 104 can be formed separately from the conduit 102, with individual needle sections 96, 96a, respectively, connected to the flow line 104 and instrument I as described above. Alternatively, as shown in FIG. 10, the compliance chamber 120 can be connected to the loop 110 at the flow splitter connection 109.

The inventions embodied in the instruments and systems described above are useful in constantly monitoring and controlling both intraocular fluid pressure and suction forces during ophthalmic surgery. By allowing the surgeon the benefit of this type of equipment much of the guesswork of maintaining optimum intraocular pressure during surgery is removed, resulting in safer and more accurate surgical procedures. Moreover, the control systems can automatically regulate intraocular pressure according to a predetermined set of commands more rapidly and accurately than possible before.

Although different embodiments of the invention may vary in detail they are still intended to be within the scope of the inventive concept described above. The details described in the foregoing preferred embodiments are intended to be illustrative and not limiting in any sense.

We claim:

1. An apparatus for measuring and automatically controlling intraocular pressure during ophthalmic procedures, comprising:
    (a) a first needle means suitable for penetrating the ocular globe, and including a first opening for communicating with the interior of the ocular globe;
    (b) a pressure sensor/transducer mounted on the first needle means outside and immediately adjacent to the ocular globe so as to communicate with the first opening for generating appropriate signals in reference to changes in intraocular pressure;
    (c) a second needle means suitable for penetrating the ocular globe, and including an opening for communicating with the interior of the ocular globe;
    (d) fluid transfer means for delivering fluid at varying rates in response to signals from the pressure sensor/transducer;
    (e) conduit means for transporting fluid between the fluid transfer means the the opening of the second needle means;
    (f) means for automatically varying and controlling the rate of fluid delivered by the fluid transfer means at a preselected level in response to signals from the pressure sensor/transducer.

2. The device of claim 1, wherein the pressure sensor/transducer means includes a flexible diaphragm and a pressure transducer in physical contact with the diaphragm for generating electrical signals in response to movement of the diaphragm caused by pressure differences in the intraocular fluid.

3. The device of claim 1, wherein the apparatus includes a chamber, an elongated needle portion with the opening therein projecting from the chamber, the pressure sensor/transducer means mounted in the chamber opposite to the opening in the elongated needle portion.

4. The device of claim 1, wherein the pressure sensor/transducer means includes a cantilevered piezo-resistive element and a pressure sensitive means in contact with each other.

5. The device of claim 1, wherein the fluid transfer means includes means for circulating fluid through the ocular globe at a predetermined rate and means for increasing or decreasing the flow rate for increasing or decreasing intraocular fluid pressure in response to changes in intraocular pressure.

6. The device in claim 1, wherein the fluid transfer means includes means for maintaining a predetermined static fluid pressure in the ocular globe, and means for supplying or removing intraocular pressure.

7. The device of claim 6, wherein the fluid transfer means further includes a conduit loop and a pump for continuously circulating fluid in the conduit loop, the conduit means connecting the conduit loop with the opening in the instrument, means for receiving the signals and changing the speed of the pump in response to predetermined changes in intraocular pressure.

* * * * *